United States Patent [19]

Kister et al.

[11] 4,020,121
[45] Apr. 26, 1977

[54] OLIGOMERIZATION REACTION SYSTEM

[75] Inventors: Albert T. Kister; Eugene F. Lutz, both of Houston, Tex.

[73] Assignee: Shell Oil Company, Houston, Tex.

[22] Filed: Dec. 15, 1975

[21] Appl. No.: 640,597

[52] U.S. Cl. .................................... 260/683.15 D
[51] Int. Cl.$^2$ .......................................... C07C 3/10
[58] Field of Search ........................... 260/683.15 D

[56] References Cited

UNITED STATES PATENTS

| | | | |
|---|---|---|---|
| 3,558,736 | 1/1971 | Bergem et al. | 260/683.15 D |
| 3,644,564 | 2/1972 | Van Zwet et al. | 260/683.15 D |
| 3,647,914 | 3/1972 | Glockner et al. | 260/683.15 D |
| 3,647,915 | 3/1972 | Bauer et al. | 260/683.15 D |
| 3,676,523 | 7/1972 | Mason | 260/683.15 D |
| 3,686,351 | 8/1972 | Mason | 260/683.15 D |
| 3,737,475 | 6/1973 | Mason | 260/683.15 D |
| 3,825,615 | 7/1974 | Lutz | 260/683.15 D |
| 3,904,547 | 9/1975 | Aycock et al. | 252/414 |

*Primary Examiner*—C. Davis

[57] ABSTRACT

Ethylene is oligomerized to even numbered alpha-monoolefins, predominantly in the range up to about $C_{40}$, by contact at elevated pressure with nickel complex catalysts dissolved in polar organic solvents, preferably certain diols. In the recovery of oligomers from the reaction product of this process, the ethylene-containing liquid oligomer product phase, after separation from the liquid solvent phase, is scrubbed with a clean portion of the organic solvent to remove catalyst complex, which may be recycled to the reaction zone. Such catalyst removal prevents polyethylene formation during further processing of the product, thus avoiding fouling of process equipment and improving ethylene utilization as well as catalyst utilization.

7 Claims, 2 Drawing Figures

OLIGOMERIZATION REACTION SYSTEM

BACKGROUND OF THE INVENTION

1. Field of the Invention

This invention relates to an improvement in a process for the production of linear alpha-olefins. More particularly, it relates to an improvement in a process for the conversion of ethylene to oligomers by contact with a catalytic nickel complex dissolved in a polar organic solvent.

2. Description of Prior Art

Linar monoolefins are compounds of established utility in a variety of applications. Terminal linear monoolefins, particularly those of 14 to 20 carbon atoms per molecule, are known useful intermediates in the production of various types of detergents.

It is known that ethylene can be oligomerized to higher molecular weight linear monoolefins. A variety of suitable oligomerization catalysts and processes are known. This invention is concerned with an improvement in oligomerization processes in which ethylene is converted to higher linear alpha-monoolefins by contact with a catalytic nickel complex dissolved in certain polar solvents.

One group of known nickel complex catalysts for ethylene oligomerization is prepared as the reaction product of a olefinic nickel compound and a suitable bidentate ligand. Olefinic nickel compounds used in the preparation os suh catalysts are zero-valent nickel compounds such as bis(cyclooctadiene)nickel(0) or $\pi$-allyl nickel compounds. Such catalysts and their use in ethylene oligomerization are described in the following patents: U.S. Pat. No. 3,644,564 to Van Zwet et al. U.S. Pat. No. 3,647,914 Glockner et al. and U.S. Pat No. 3,647,915 to Bauer et al.

In a different method of preparing similar nickel complex catalysts, the complex is prepared by contacting in certain polar organic solvents in the presence of ethylene (1) a simple divalent nickel salt which is at least somewhat soluble in the solvent (2) a boron hydride reducing agent and (3) a suitable bidentate ligand. Preparations of catalysts of this type and their use in ethylene oligomerization are described in the following U.S. Pat. Nos. 3,676,523; 3,686,351 and 3,737,475, all to R. F. Mason and 3,825,615 to Lutz.

SUMMARY OF THE INVENTION

In the process separation. the recovery of olefins from the product of oligomerizing ethylene by contact with a solution of a nickel complex in a polar organic solvent, which is improved according to this invention, the hydrocarbon product is separated from the predominant portion of solvent and catalyst by a liquid-liquid phase separation Although the nickel catalyst is preferentially soluble in the polar solvent, it has been found that small but significant quantities of nickel catalyst are retained in the hydrocarbon product layer. This is due primarily to solubility of some of the nickel complex and solvent in the hydrocarbon phase at the elevated reaction pressure, and secondarily to possible entrainment of catalyst-contining solvent. The hydrocarbon phase of the obligomerization reaction product also contains a substantial proportion of dissolved ethylene, which is retained until the hydrocarbon phase is deethenized.

The nickel complex obligomerization catalysts are capable of producing not only oligomeric linear alpha-olefins, but also, under certain conditions, significant amounts of ethylene polymers having molecular weights from a few thousand to as high as a few million. Such polymeric product is referred to herein as "polyethylene," in contrast to the lower products of up to about 100 carbon atoms per molecule, which are "oligomers." Production of polyethylene is particularly favored when ethylene and nickel complex catalyst are present in a hydrocarbon medium in which the complex is insoluble or when ethylene is present in a vapor space in which droplets of catalyst solution are also present or whose walls are splashed with catalyst solution, especially at conditions at which the catalyst solution is relatively concentrated. It has been found that, if catalyst, solvent and ethylene are present in the hydrocarbon product phase at conditions under which part of the hydrocarbon is removed by flashing or distillation, some of the ethylene is converted to polymeric polyethylene. As produced in the oligomerization process, such polyethylene is not a usable commercial product and thus results in decreasing the yield of desired product from the ethylene feed. It has an even more objectionable effect in that it tends to rapidly foul mechanical equipment downstream from the reactor.

We have found it to be important for effective operation of a process in which ethylene is converted to linear alpha-monoolefin oligomers by contact with a nickel complex in a suitable organic polar solvent at elevated pressure to remove active catalyst residue from the hydrocarbon product of the process as soon as possible. This not only prevents the formation of polyethylene in the crude product stream with avoidance of the attendant difficulties just described, but has the following further advantages. It permits obtaining an improved yield, based on fresh ethylene feed to the process. It results in an increased yield of oligomer product per pound of catalyst, since the catalyst complex scrubbed from the product can be returned to the reaction zone. It results in improved product quality, i.e., higher alpha-monoolefin content, since the presence of the catalyst in the crude product causes isomerization of the alpha- to internal olefins, branching and production of heavy ends. The prevention of formation of polyethylene in the downstream equipment, of course, results in the improved operability of the process and in higher stream factor and reduced maintenance and operating costs, since it reduces or avoids the need for process downtime to remove polymer deposits from the equipment.

According to this invention, catalyst residue is removed from the hydrocarbon product phase of a process in which ethylene is oligomerized to higher alpha-monoolefins by contact with a nickel complex in a suitable polar organic solvent at elevated pressure, by subjecting the hydrocarbon phase to a scrubbing step utilizing the same type of polar organic solvent, prior to the time that the catalyst-contaminated hydrocarbon phase is subjected to depressurization for removal of ethylene.

In the best mode contemplated for practicing the invention, the solvent employed for scrubbing catalyst residue from the oligomerization product is a diol, the same solvent employed in the oligomerization step, and is suitably obtained by purifying a bleed stream of the solvent phase separated from the reaction mixture. The scrubber extract contains active catalyst and may suitably be returned to the catalyst preparation step or to the oligomerization reaction zone. A particularly preferred solvent in the process of this invention is 1,4-butanediol.

DESCRIPTION OF THE INVENTION

Figure 1:
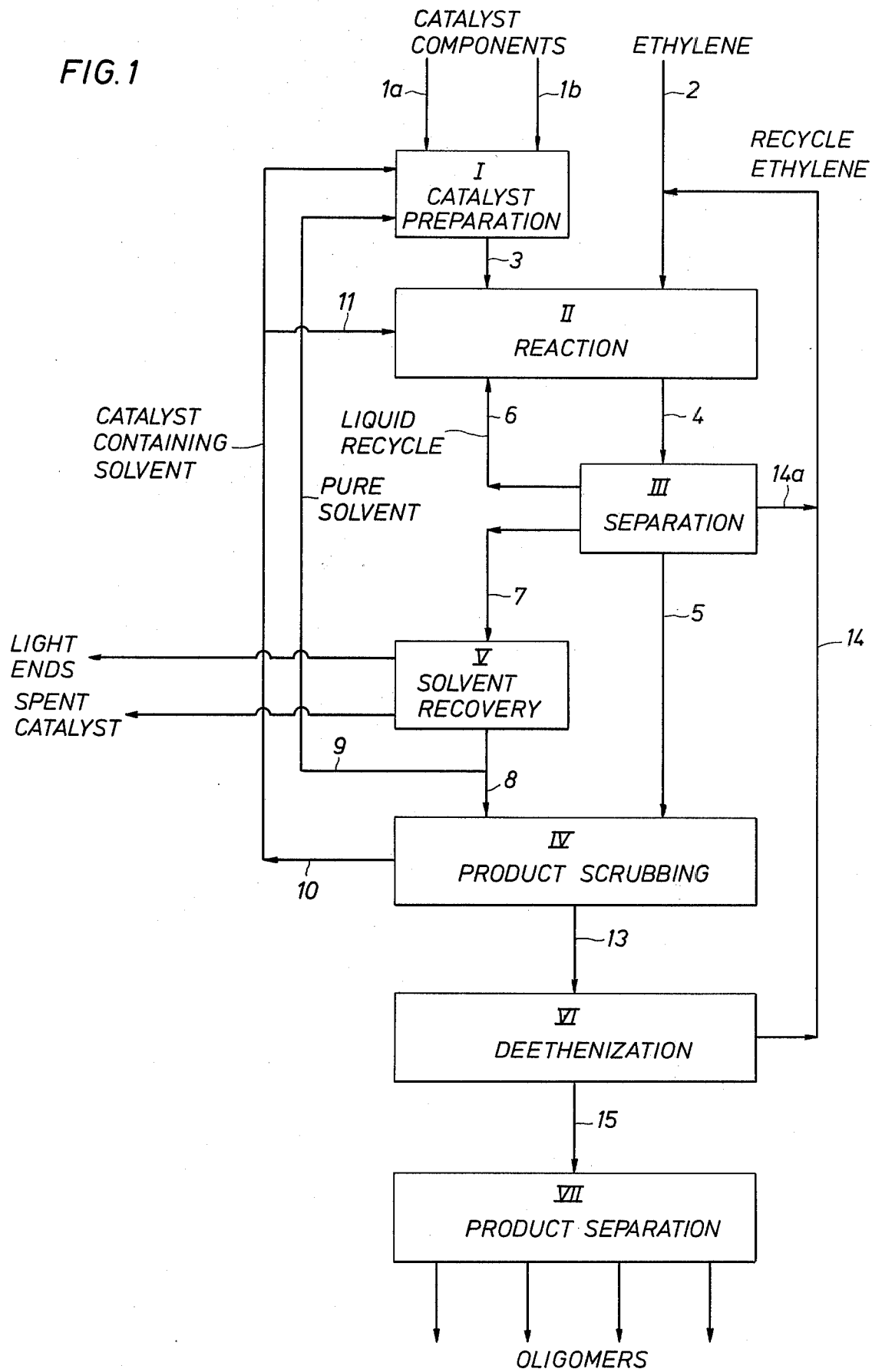
FIG. 1 is a process flow diagram of the process of the present invention.

Oligomers of monoolefins are addition products which contain two or more monomer units, but not as many as the relatively high molecular weight addition products which are referred to as polymers. The present invention is concerned with a process for the production of oligomers of ethylene. The process is particularly adapted for the production of linear, terminally unsaturated oligomers of ethylene containing from 2 to about 20 monomer units.

References disclosing a variety of ethylene oligomerization catalysts which are suitable for the use in the process of this invention have been referred to in the discusion of the prior art. In the preferred oligomerization reactions utilized in the process of this invention, the oligomer product contains all even carbon number olefins from butene to as high as can be determined by analytical procedures, in a geometric distribution pattern which, for any given product, can be defined by a single constant, referred to as the "product distribution" constant or K factor, according to the mathematical expression:

$$K = \frac{\text{Moles of } C_{n+2} \text{ Olefin}}{\text{Moles of } C_n \text{ Olefin}} ; \text{(for } n = 4, 6, 8 \ldots \text{)}.$$

The product distribution constant is affected by a number of factors, including the type of bidentate ligand employed in the catalyst complex, the reaction solvent or diluent, the reaction conditions of temperature and pressure, the catalyst concentration in the solvent, and the degree of ethylene saturation of the reaction solution.

Intermediate alpha-olefins in the range from $C_{12}$ to $C_{18}$ are particularly desirable commercial products. When the oligomerization catalyst and conditions are selected to produce a relatively high yield of $C_{12}$-$C_{18}$ oligomers in the reaction step — conditions at which the product distribution constant is below about 0.9 — it will be found that the product distribution is such that neglible amounts of polymer having, say, a hundred or more monomer units per molecule, are produced. Such total oligomerization reaction products are hydrocarbon mixtures which are liquid at the reaction conditions of pressure and temperature further discused below. Such minimal amounts of polymer as may be produced in the reaction remain in the reaction product and create no problems in the process.

Catalysts:

The catalysts suitable for use in the process of this invention are complexes of nickel compounds with a bidentate chelating ligand, which are prepared by reacting a suitable bidentate ligand with an olefinic nickel compound such as bis(cyclooctadiene)nickel(0) or with a simple divalent nickel salt and boron hydride reducing agent in the presence of ethylene in a suitable polar organic solvent. Preparation and use of catalysts of the former type are described in U.S. Pats. 3,644,564 to Van Zwet et al. 3,647,914 to Glockner et al. and 3,647,915 to Buer et al. Preparation and use of catalysts of the latter type ae described in U.S. Pats. Nos. 6,676,523 3,686,351 and 3,737,475, all to R. F. Mason and 3,825,615 to Lutz. The disclosures of all of said patents with respect to the components, preparation and use of such catalysts are incorporated herein by reference.

The nickel complexes which act as oligomerization catalysts comprise an atom of nickel chelated with a bidentate chelating ligand. Preferred bidentate legands are those having a tertiary organophosphorus moiety with a suitable functional group substituted on a carbon atom attached directly to or separated by no more than two carbon atoms from the phosphorus atom of the organophosphorus moiety. Representative ligands of this type are compounds of the general formula

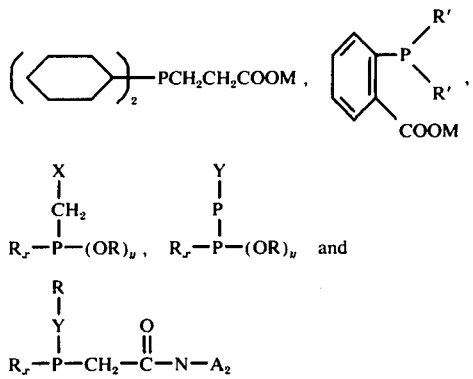

wherein R, independently, lis a monovalent organo group, R' a monovalent hydrocarbyl group; X is carboxymethyl or carboxyethyl; Y is hydroxymethyl, mercaptomethyl, hydrocarboyl of up to 10 carbon atoms or hydrocarbyloxycarbonyl of up to 10 carbon atom; A is hydrogen or an aromatic group of up to 10 carbon atoms; M is hydrogen or an alkali metal, preferably sodium or potassium; x and y are zero, one or two and the sum of x and y is two, with the proviso that when x is two the R groups my together with the phosphorus atom form a mono- or bicyclic heterocyclic phosphine having from 5 to 7 carbon atoms in each ring thereof. Particularly preferred complexes are those described in U.S. Pat. No. 3,676,523 in which the ligand is an o-dihydrocarbylphosphinobenzoic acid or its alkali metal salt and most preferably o-diphenylphosphinobenzoic acid; in another preferred complex described in U.S. Pat. No. 3,825,615, the ligand is dicyclohexylphosphinopropionic acid or its alkali metal salt.

Although it is not desired to be bound by any particular theory, it appears likely that the catalyst molecule undergoes chemical transformation during the course of the oligomerization reaction, possibly involving coordination and/or bonding of ethylene to the nickel moiety. However, it appears likely that the bidentate chelating ligand remains complexed and/or chemically bonded to the nickel moiety during the course of the oligomerization reaction and that this complex of the nickel and the chelating ligand is the effective catalytic species of the oligomerization process. In any event, the bidentate ligand, such as the phosphorus-containing chelating ligand, is an essential component of the catalyst and, provided the nickel catalyst contains the required bidentate ligand, the nickel catalyst may be complexed with a variety of additional oganic complexing ligands.

The molar ratio of nickel to bidentate ligand in the preparation of the nickel complex catalyst is preferably at least 1:1, i.e., the nickel is present in equimolar amount or in molar excess. In the preparation of catalyst complexes from a nickel salt, a ligand and boron hydride reducing agent, the molar ratio of nickel salt to ligand is suitably in the range from 1:1 to 5:1 with molar ratios of about 1.5:1 to 3:1 preferred and ratios of about 2:1 especially suitable. In these preparations, the boron hydride is suitably present in equimolar amount or molar excess relative to the nickel salt. There does not appear to be a definite upper limit on the boron hydride/nickel ratio, but for economic reasons it is preferred not to exceed a ratio of 15:1; the preferred ratio is usually between about 1:1 and bout 10:1 with a ratio of about 2:1 specially preferred; ratios somewhat below 1:1 are also suitable.

The nickel complex catalysts are suitably preformed by contacting the catalyst precursors in the presence of ethylene in a suitable polar organic diluent or solvent, preferably a polar organic diluent or solvent employed for the oligomerization process, which is not reduced by the boron hydride reducing agent. In a preferred modification of producing the preferred catalyst complexes as detailed in the patents to Mason and Lutz, supra, the solvent, nickel salt and ligand are contacted in the presence of ethylene before the addition of boron hydride reducing agent. It is essential that such catalyst compositions be prepared in the presence of ethylene. The catalysts are suitably prepared at temperatures of about 0° to 50°C, with substantially ambient temperatures e.g., 10 °–30° C preferred. The ethylene pressure and contacting conditions should be sufficient to substantially saturate the catalyst solution. For example, ethylene pressures may be in the range from 10 to 1,500 psig or higher. Substantially elevated ethylene pressures, e.g., in the range from 400 to 1,500 psig are preferred.

Solvents:

While the nickel complex catalysts described above are effective oligomerization catalysts in a variety of solvents, not all solvents provide equally desirable results in utilizing the systems for the production of oligomers.

An essential requirement is that the catalyst complex be soluble in the reaction solvent. When the complexes precipitate as they tend to do in aliphatic hydrocarbon diluents, the rsulting heterogeneous systems tend to favor the production of polymer.

In order to be useful in the process of this invention, the solvent must be substantially insoluble in the hydrocarbon paoduct phase which is present in the reactor and which consists of the total oligomer product having ethylene dissolved therein. Solubilities of less than 1% by weight and preferably less than about 0.5% by weight are acceptable.

A further necessary characteristic of solvents for use in this invention is that they must be capable of preferentially dissolving the nickel complex catalyst.

The solvent should, of course, be a liquid at the reaction conditions of temperature and pressure. Its atmospheric boiling point should be at least about 75°C and may suitably be above 150°C.

It is further preferred that the solvent for use in this invention be water-soluble so that dissolved and entrained solvent can be scrubbed out of the reaction product by water wash.

Suitable solvents for use in the process of this invention are oxygen-containing polar organic compounds which meet the criteria set out above. Preferred members of this group are aliphatic diols of 2 to 7 carbon atoms per molecule, including vicinal alkane diols and alpha-omega alkane diols, the latter being preferred. 1.4-Butanediol is especially preferred. The term "butanediol", as employed herein, refers to 1,4-butanediol. Alkylene carbonates are another group from which suitable solvents for this reaction may be selected, e.g., 1,2propylene carbonate. Solvents may be used in admixture.

Process:

The major steps of the process of this invention consist of catalyst preparation, reaction, separation of the reactor effluent into a liquid product for work-up and solvent phase of which part is recycled and part is purified by fractionation, scrubbing of the product phase to remove residual catalyst therefrom, deethenization of the scrubbed product, and further work-up of the deethenized product to separate it into desired product fractions. An optional but preferred step is separate removal of entrained gaseous ethylene from the reactor effluent prior to liquid pahse separation.

Sutiable methods for preparing the catalyst complex and for conducting the oligomerization reaction as sufficiently described in the above referred-to patents and are now well known to persons skilled in this art. A preferred method is described in the illustrative example below.

In summary, the oligomerization reaction may be conducted at temperaturs in the range from about 25°C to 150°C, but preferably from about 70° to 100° C. The pressure must be at least sufficient to maintain the reaction mixture substantially in liquid phase although excess ethylene will be present in vapor phase. Pressures in the range from about 300 to 5,000 psig may be employed. Other than for maintaining the liquid phase condition of the system, the total pressure is less significant than the partial pressure of ethylene, which is a primary factor in maintaining the desired ethylene concentration in the solvent phase where the oligomerization reaction takes place. In the preferred system, the ethylene partial pressure is suitably in the range from about 400 to 2,500 psig and preferably between about 1,000 and 2,500 psig. The concentration of catalyst, calculated as nickel metal, in the solvent phase is at least about 0.001 molar and suitably from about 0.001 to 0.005 molar.

While the oligomerization reaction can be carried out in batch or continuous manner, this invention is concerned with a continuous process in which catalyst and ethylene are continuously charged to the reaction zone and a portion of the hydrocarbon product is continuously separated from the reaction mixture and removed for work-up. In the preferred system, the reaction mixture is continuously circulated through a reaction loop consisting of a reaction zone and a separation zone, as described in further detail below.

In conducting the oligomerization process with a preferred nickel complex catalyst in butanediol solvent, it was found that the liquid oligomer phase recovered from the product separator still contained small amounts of active nickel complex. The product also contained a substantial amount of ethylene in solution. During the work-up of the oligomer product, dissolved ethylene is removed, as by flashing or fractionation. It was discovered that when ethylene is removed from the hydrocarbon product, dissolved catalyst and solvent separated to form a catalyst solution with a substantially higher catalyst concentration than the original reaction catalyst solution. The presence of such solution in the ethylene-containing product resulted in the formation of higher molecular weight products, including significant amounts of ethylene polymer having molecular weights in the range from $6 \times 10^3$ to $6 \times 10^6$. This polymer tended to separate out and deposit on parts of the product work-up apparatus. In a continuously operating system, the polymer deposits were such that the process had to be interrupted frequently for removal of polymer from the equipment, with consequent very poor process stream factor.

It was then found that the problem of polymer formation and deposition in the product work-up system can be overcome, and other advantages listed above can be obtained, by practicing according to the process of the present invention. In accordance with this invention, the reaction product is processed as follows:

The reaction mixture as withdrawn from the reactor contains three phases: (1) a liquid solvent phase in which catalyst is dissolved; (2) a liquid hydrocarbon phase which consists of total oligomer and includes dissolved ethylene, solvent and nickel complex catalyst and (3) gaseous ethylene. It is preferred to subject such reactor effluent to degassing, i.e., separation of physically entrained ethylene gas from the two liquid components of the mixture. This ethylene is preferably recycled to the reactor. At least part of the degassed liquid is then separated into a solvent phase which contains active catalyst complex and a product phase.

A substantial portion of the solvent phase is recycled to the reactor and part is passed to a solvent recovery zone in which purified solvent is produced.

The separated product phase is passed to a product scrubber, in which a stream of pure solvent obtained from the solvent recovery zone contacts the product stream in countercurrent flow and serves to remove residual active catalyst complex.

The solvent extract from the product scrubber may be returned to the catalyst preparation or reaction zones.

The product leaving the scrubber is substantially free of active catalyst complex. It may contain individual inactive catalyst components, incluing nickel and phosphorus compounds, but not in the form of an active catalyst complex. When properly scrubbed, the reaction product composition remains substantially unchanged during further downstream processing. The product is first passed to a deethenizer for removal of ethylene which may suitably be returned to the reactor. The deethenized product is suitably water-scrubbed for removal of dissolved and entrained solvent carried over from the product scrubber and is then subjected to a series of appropriate fractionations for recovery of desired oligomer fractions.

DESCRIPTION OF THE DRAWING

The invention will be described in further detail by reference to the drawing.

FIG. 1 of the drawing is a process flow diagram showing the process of this invention in its broadest aspect. A nickel comlex catalyst is prepared in catalyst preparation zone I to which the various catalysts components required for catalyst preparation are added through lines represented by 1a, 1b, 9 and 10. The oligomerization reaction takes place in reaction zone II, to which ethylene, including recycle ethylene from lines 14 and 14a, is introduced through line 2 and a catalyst stream through line 3. The reaction product is passed through line 4 to separation zone III, where and ethylene gas phase, a liquid hydrocarbon phase and liquid solvent phase are separated. Ethylene is recycled to the reaction zone via lines 14a, 14 and 2. Hydrocarbon phase is recovered and passed through line 5 to product scrubber IV. Solvent phase, which may be admixed with hydrocarbon liquid, is withdrawn through line 6 and is returned as recycle to the reaction zone; part of the solvent phase removed from separation zone III is passed via line 7 to solvent recovery zone V for further work-up.

In solvent recovery zone V, the portion of the recovered solvent phase from zone III is subjected to fractionation. Streams leaving solvent recovery zone V, in addition to the purified solvent, are a spent catalyst discard stream and a light ends fraction. Part of the clean solvent from zone V is passed through line 8 to product scrubber IV and part may be passed to catalyst preparation zone I via line 9.

In product scrubber IV, the liquid hydrocarbon phase from separation zone III is treated with clean organic polar solvent from solvent recovery zone V to remove residual catalyst components.

The scrubber extract, consisting of solvent and extracted catalyst, is removed via line 10. It may be returned to reaction zone II via line 11 or to catalyst preparation zone I or partly to each.

The clean hydrocarbon product from which catalyst residue has been removed is passed via line 13 to deethenizer VI, in which the remaining ethylene is removed for return via line 14 to the ethylene feed line to the reaction zone. The deethenized product passes through line 15 to product separation zone VII in which residual solvent is removed and they hydrocarbon product is separated into suitable olefin fractions.

A preferred mode of practicing the process of this invention is described by reference to FIG. 2 of the drawing. Identical numerals are employed as in FIG. 1 to the extent that it is appropriate.

Catalyst components are added through lines 1a and 1b to catalyst preparation zone I. It is preferred to employ pure solvent, returned from solvent recovery zone partly to V via line 9, in the preparation of catalyst component concentrates and dilute these with scrubber extract obtained from zone IV via line 10. Fresh ethylene enters the reaction system through line 2.

The reaction loop consists of reaction zone II and separation zones IIIA and IIIB. The reaction zone may contain as reactor a pipeline reactor or a series of agitated pressure vessels. The reaction mixture is continuously circulated through the reaction loop. Suitable reaction conditions include a temperature between 70° and 100° C and a substantially elevated pressure, e.g., between about 1,200 and 1,500 psig ethylene partial pressure. At steady state conditions in a continuous process, the reaction mixture consists of a liquid solvent phase containing dissolved catalyst complex and ethylene, a liquid product phase consisting essentially of a major amount by weight of oligomer and a minor amount of dissolved ethylene, and an ethylene gas phase. The liquid entering the reactor consists of the recycle stream from line 6 which, at steady state, contains about 4 parts by weight of solvent phase per one part of liquid product phase, plus makeup catalyst added from zone I via line 3 and ethylene, including fresh and recycle ethylene, added via line 14, the gas being compressed to reaction pressure by compressor 14x. It is not necessary to have liquid hydrocarbon phase present in the reaction zone. At startup, the reaction liquid may consist exclusively of the solvent phase.

Total reaction mixture passes from the reaction zone through line 4 to a gas separator IIIA, which is operated at about reaction pressure and at a temperature that is not significantly higher than that in the reaction zone. That part of the ethylene which is present in the reaction effluent in the vapor phase is separated in gas separator IIIA and returned via line 14a to recycle ethylene line 14. Gas separator bottoms, consisting of the total liquid reactor effluent, is passed via line 4a to phase separation zone IIIB. The solvent phase or a solvent hydrocarbon mixture removed from zone IIIB is pumped through line 6 for return to the reaction zone. The hydrocarbon phase, containing the olefinic rection product, dissolved ethylene and disolved and entrained solvent and catalyst components, passes via line 4b to a second liquid-liquid phase separation zone IIIC in which the remaining amount of polar solvent, including a substantial part of the residual catalyst is recovered and removed via line 7 to solvent recovery zone V.

The recovered product, which still contains small amounts of solvent and catalyst complex, passes from product separation zone IIIC via line 5 to product scrubber IV, in which the residual amount of catalyst is scrubbed out of the product by olvent obtained from solvent recovery zone V through line 8 and 8a. The scrubbed product passes through line 13 to deethenizer VI in or ahead of which the pressure is substantially lowered and the remaining amount of ethylene is removed for return to the reaction zone via line 14. The deethenized product passes through line 15a to a water scrubber VIII in which final trace amounts of solvent are scrubbed out by means of water which enters the column through line 18. The clean deethenized crude oligomer product leaves the water scrubber through line 15b and is passed to appropriate equipment for separation into desired fractions.

The water scrubber extract passes through line 16 to a solvent dehydrator IX in which solvent is separated from the water, suitably by fractionation; the water is returned via line 18 to the water srubber and the solvent via line 17 to solvent recovery zone V. Light ends and spent catalyst are removed as separate streams from the solvent recovery zone; clean solvent from zone V is employed to scrub catalyst residue from the reaction product in scrubber IV, as explained above, and in the preparation of make-up catalyst.

It is known from the references discussed above, and from general considerations with which chemical engineers are familiar, how to conduct the above-described process in terms of suitable reactants, apparatus and conditions. In the description of the schematic flow diagram, detans such as valving, piping, pumps, instrumentation and the like which will be apparent to persons skilled in the art have been omitted. It will also be apparent that various modifications in the process steps can be made without departing from the scope of the present invention.

Conditions for practicing the process of this invention are illustrated in the following example.

ILLUSTRATIVE EXAMPLE

This example is described with reference to FIG. 2 of the drawing.

Catalyst is prepared by combining in a vigorously stirred autoclave in catalyst preparation zone I a solution of nickel chloride hexahydrate and diphenylphosphinobenzoic acid in 1,4-butanediol, saturated with ethylene at catalyst preparation pressure, added through line 1a, with an aqueous solution of sodium borohydride and potassium hydroxide added through line 1b. Suitable conditions include a temperature of about 40° C, 1300 psig pressure, and a residence time of 3 to 5 minutes. In continuous opration of the oligomerization process, a concentrate of the nickel salt and ligand is prepared in pure butanediol, e.g., a portion of that removed from solvent recovery zone V through lines 8 and 9 and combined with additional butanediol solvent obtained as the scrubber extract from zone IV via line 10.

The reaction zone comprises an externally cooled pipeline reactor. Makeup ethylene and recycle ethylene are combined and charged to the reactor at a pressure of 1400 psig. The ethylene is injected into the catalyst recycle stream near the place where it enters the reactor. Catalyst solution is also injected into the recycle stream, preferably following the ethylene injection point.

During continuous operation, the reaction mixture in the reaction zone consists of a liquid solvent phase, a liquid hydrocarbon product phase and gaseous ethylene. The solvent phase contains the nickel complex catalyst and is saturated with dissolved ethylene. In the reaction liquid, the catalyst solution in butanediol is the continuous phase and the hydrocarbon liquid the dispersed phase. The hydrocarbon phase consists of about 75% by weight oligomer product saturated with about 25% dissolved ethylene.

The reaction mixture is continuously circulated through a reaction loop consisting of the pipeline reactor, gas-liquid separator IIIA, liquid-liquid separator IIIB and the circulating pump, all interconnected by pipe. Turnover time for the reaction fluid is about 1 minute. The reaction zone is maintained at about 90° C by external cooling, as required, and at a pressure of about 1400 psig, maintained by the circulating pump in the catalyst recycle line and controlled by venting excess ethylene from separator IIIA on pressure control.

Gas separator IIIA is suitably a cyclone type vessel in which ethylene is taken overhead and the total liquid mixture is removed and passed to phase separator IIIB. Vessel IIIB is suitably a hydroclone in which the major portion of the solvent phase present in the reaction mixture, which may also contain entrained hydrocarbon phase, is removed for immediate return to the reactor and a hydrocarbon product phase, containing entrained solvent phase, is taken overhead to a second separator vessel IIIC in which further phase separation takes place, removing additional solvent phase which is passed to the solvent recovery zone.

A portion of the solvent phase, carefully separated from entrained hydrocarbon liquid and gas, is subjected to purification in solvent recovery zone V. This consists, suitably, of a vacuum distillation column in which purified butanediol is taken as a side stream. Spent catalyst is removed as a bottoms stream and the overhead consists of water and a small amount of light ends which are formed during distillation. At 20 millimeter mercury top pressure, the top temperature of the column is about 80° C and the bottom temperature is about 140° C.

The hydrocarbon product phase obtained from zone IIIC is scrubbed in product scrubber IV with pure butanediol from the solvent recovery column. The scrubber is suitably a column packed with porcelain packing, such as three-quarter-inch saddles. The upper and lower sections are unpacked to serve as disengaging sections for scrubbed oligomer and butanediol extract. The scrubber suitably operates 90°–95° C and 1100–1150 psig, i.e., about 250 to 300 psig below the reactor pressure of 1,400 psig. Purified butanediol is fed at the top of the packing on level control to hold the butanediol hydrocarbon interface above the packing. The hydrocarbon product is introduced below the packed section, is dispersed in the butanediol by the packing, and is coalesced above the packed zone. The hydrocarbon is discharged on pressure control from the top of the scrubber and flows to a product surge vessel, not shown on FIG. 2, from which it is then charged to the deethenizer, a water scrubber and further product work-up.

The quantity of butanediol used for scrubbing is adjusted by flow control of the butanediol scrubber extract from the bottom of the scrubber. The extract is passed to a settling vessel, not shown, to disengage entrained oligomer, and then pumped to the catalyst preparation unit.

The quantity of butanediol used for scrubbing may be adjusted to represent a fixed proportion, e.g., 90% by volume, of the makeup catalyst. The amount of butanediol employed for scrubbing the oligomer product suitably is about 10 to 15% by volume of the product stream. The scrubber may be operated at 50° to 120°C and preferably at about 90° to 100°C. The scrubber is preferably operated at about the pressure maintained in the reaction system, less the pressure drop through the downstream equipment between reactor and scrubber; the pressure should remain at least sufficient to maintain dissolved ethylene in solution.

In a typical operation of such a system, the crude product stream charged to this scrubber contains 7 to 9 ppm phosphorus and 3 to 5 ppm nickel, basis room temperature weathered oligomer. In the scrubber, about 35% of the phosphorus and 75 to 80% of the nickel is extracted. Based on comparison of elemental phosphorus and trivalent phosphorus analysis, the extracted phosphorus appeared to be active liquid and the non-extractable phosphorus appeared to be a decomposition product of ligand. The phosphorus and nickel in the butanediol extract represented about 30% and 10%, respectively, of the makeup phosphorus and nickel charged to the catalyst preparation unit.

In a number of runs carried out at different conditions it was confirmed that it is not the absolute level of nickel and phosphorus in the oligomer product which is critical to effective product cleanup, but the removal of active catalyst complex which contains both nickel and phosphorus. Thus, for example, the concentration of nickel in the crude product may be in the range from 3 to 12 ppm, reduced by scrubbing to the range of 1 to 6 ppm and the phosphorus concentration from about 6 to 13 ppm in the crude product, reduced by scrubbing to about 5.5 to 12.4 ppm. In spite of the fact that significant concentrations of nickel and phosphorus remained in the scrubbed product, it was found that scrubbing of the oligomer product with diol completely prevented polymer deposition in the equipment downstream from the product scrubber.

Figure 2:
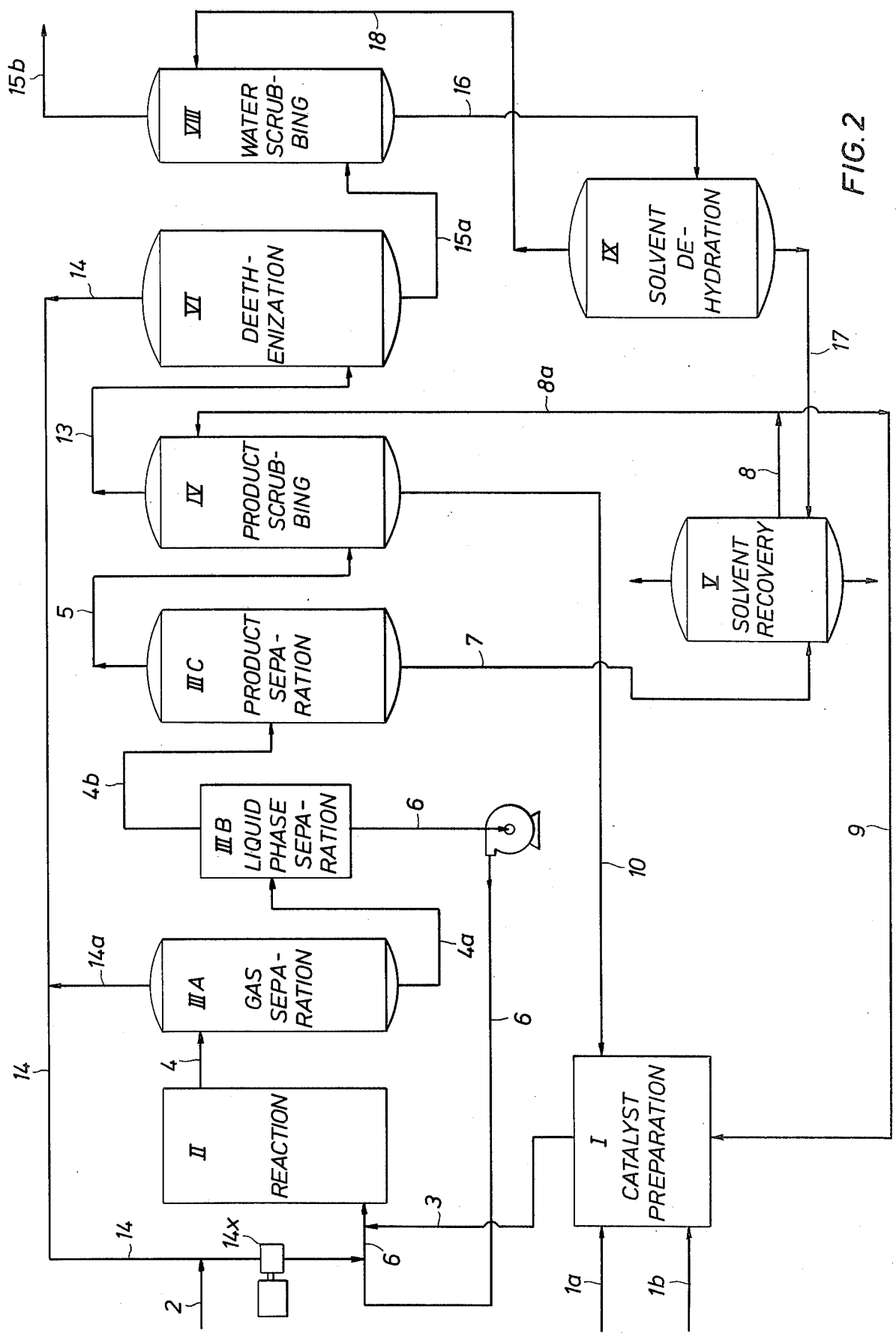
FIG. 2 is a schematic flow diagram illustrating a preferred mode of practicing the process of this invention.

The scrubbed oligomer from the scrubbing column is reduced in pressure from about 1100 psig to 150 psig and accumulated in a flash vessel which is the equivalent of deethenizer VI shown in FIG. 2. If a simple flash vessel is employed, the vapors flashed consist predominantly of ethylene and butylene and may be charged to a debutenizer column, which is part of the product work-up system, rather than being recycled directly as shown in FIG. 2. The liquid oligomer is water-scrubbed in scrubber VIII to remove dissolved and entrained butanediol and traces of catalyst component residues. The water-scrubbed oligomer is then passed to the product work-up system, which suitably consists of a series of fractionating columns.

When the reaction system was operated without product scrubber IV, i.e., by passing the product from the product separator directly to the deethenizer, it was found that removal of ethylene threw out of solution a small amount of butanediol phase wherein catalyst was concentrated up to three times the level in the reaction catalyst solution. This resulted in significant amounts of polymer being deposited in the ethylene flash accumulator where the oligomer product was deethenized while being reduced in pressure. The butanediol scrubber, by removing active catalyst from the oligomer, completely prevented polymer formation in the ethylene flash accumulator.

We claim as our invention:

1. In the process for the oligomerization of ethylene to linear alpha-olefins wherein (1) ethylene is oligomerized by contact in liquid phase at elevated pressure with a solution of an oligomerization catalyst composition comprising catalytically active nickel complex in a polar organic solvent; (2) at least part of the resulting reaction product is separated at elevated pressure into a liquid solvent phase and a liquid hydrocarbon product phase containing dissolved ethylene, catalyst and solvent; and (3) said product phase is separated into unreacted ethylene and ethylene oligomers, the improvement which comprises scrubbing said hydrocarbon product phase, after separation from the solvent phase and while at sufficiently elevated pressure to maintain said ethylene dissolved therein, with sufficient polar organic solvent to remove the residual amount of catalytically active nickel complex from said product phase.

2. Process according to claim 1 wherein the solvent employed in said scrubbing step is the same as the solvent employed in the oligomerization reaction.

3. Process according to claim 2 wherein the solvent extract from said scrubbing step is returned to the oligomerization reaction zone.

4. Process according to claim 3 wherein said extract is employed in the preparation of additional oligomerization catalyst.

5. Process according to claim 2 wherein said solvent is 1,4-butanediol.

6. In the process for the oligomerization of ethylene to linear alpha-olefins wherein
 1 a nickel complex catalyst solution in a diol solvent is prepared in a catalyst preparation zone;
 2 ethylene is contacted with said catalyst solution in a reaction zone at a temperature in the range from about 25° to 150° C at a partial presure of ethylene in the range from 400 to 2,500 psig;

3. a portion of the reaction mixture is continuously removed from the reaction zone and gaseous ethylene separated therefrom for recycle to the reaction zone;
4. at least part of the liquid reaction mixture, after ethylene removal, is separated in a solvent/product separation zone into a liquid solvent phase and a liquid hydrocarbon product phase containing dissolved ethylene, catalyst and solvent;
5. said separated product phase is deethenized;
6. the separated ethylene is recycled to the reactor and;
7. oligomer fractions are recovered from the deethenized product; wherein the system is maintained at substantially superatomspheric pressure, sufficient to maintain dissolved ethylene in solution in the hydrocarbon phase, from the reaction zone through the deethenization zone, the improvement which comprises 1. removing a bleed stream of solvent phase from the solvent/product separation zone and subjecting it in a solvent purification zone to fractionation for recovery of a purified solvent stream;
2. passing the liquid hydrocarbon product stream from said solvent/product phase separation to a scrubbing vessel;
3. in said scrubbing vessel, passing said liquid hydrocarbon product stream countercurrently to a sufficient amount of liquid purified solvent from said solvent purification zone to remove the residual amount of nickel complex from said product stream;
4. recovering solvent, containing catalyst complex, from said scrubbing vessel and returning it to the catalyst preparation zone;
5. deethenizing the catalyst-free product stream recovered from said scrubbing vessel
6. passing the deethenized product to a second scrubbing zone in which it is contacted countercurrently with water to remove residual diol solvent;
7. dehydrating the aqueous solvent stream removed from acid second scrubbing zone and returning resulting dehydrated solvent to said solvent purification zone; and
8. passing the water-scrubbed product to a product work-up zone wherein oligmer fractions are recovered.

7. The process according to claim 6 wherein said diol is 1,4-butanediol.

* * * * *